(12) United States Patent
Aradi et al.

(10) Patent No.: US 7,462,725 B2
(45) Date of Patent: Dec. 9, 2008

(54) CHLOROMETHYLATION OF THIOPHENE

(75) Inventors: Mátyás Aradi, Budapest (HU); Ferenc Bakos, Budapest (HU); Zsolt Dombrády, Budapest (HU); Antal Gajáry, Budapest (HU); István Gyöngyösi, Budapest (HU); Ferenc Kovács, Budapest (HU); Andrea Major, Budapest (HU); Erika Máténé Török, Nagytarcsa (HU); Zsolt Párkányi, Budapest (HU); László Schultz, Budapest (HU); Attila Supic, Budapest (HU); Sándor Szabó, Budapest (HU); Erzsébet Szalay, Budapest (HU); József Ugrics, Budapest (HU); József Zsiga, Dunakeszi (HU)

(73) Assignee: Sanofi-Aventis, Paris (FR)

( * ) Notice: Subject to any disclaimer, the term of this patent is extended or adjusted under 35 U.S.C. 154(b) by 867 days.

(21) Appl. No.: 10/478,238

(22) PCT Filed: May 16, 2002

(86) PCT No.: PCT/HU02/00042

§ 371 (c)(1),
(2), (4) Date: May 27, 2004

(87) PCT Pub. No.: WO02/094806

PCT Pub. Date: Nov. 28, 2002

(65) Prior Publication Data

US 2006/0161008 A1   Jul. 20, 2006

(30) Foreign Application Priority Data

May 22, 2001   (HU) .................................. 0102118

(51) Int. Cl.
*C07D 333/12*   (2006.01)
(52) U.S. Cl. ........................................................ 549/29
(58) Field of Classification Search .................... 549/29
See application file for complete search history.

(56) References Cited

U.S. PATENT DOCUMENTS 2,527,680 A   10/1950   Kyrides et al.
4,501,903 A   2/1985   Mirviss

OTHER PUBLICATIONS

Shah et., J. Indian Chem. Soc. (1962), vol. 39(8), p. 507-510.*
Dermer et al., J. Am. Chem. Soc. (1952), vol. 74, pp. 3417-3418.*

* cited by examiner

*Primary Examiner*—Taofiq A Solola
(74) *Attorney, Agent, or Firm*—Paul R. Darkes; Paul E. DuPont

(57) ABSTRACT

The process according to the invention relates to the preparation of 2-chloromethyl-thiophene of the formula (I). During this process thiophene is chloromethylated in the presence of one or more compounds containing keto group and optionally it is transformed into the compound of the formula (II). Compounds of formula (I) and (II) are intermediates of several pharmaceutically active ingredients.

8 Claims, 1 Drawing Sheet

(I)

(II)

(III)

(IV)

CHLOROMETHYLATION OF THIOPHENE

Figure 1:
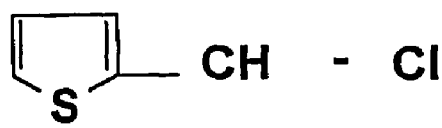

This invention relates to a new process for the preparation of 2-chloromethyl-thiophene of the formula (I)

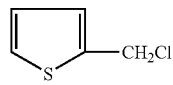

(I)

and for the preparation of 2-thienyl-acetonitrite of formula (II) starting from thiophene

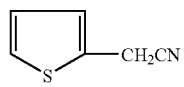

(II)

The compounds of formula (I) and (II) are valuable intermediates for the pharmaceutical industry. For example, 2-thienyl-ethylene of formula (III) prepared therefrom is the starting material for several Active Pharmaceutical Ingredients (API's).

The compound of the formula (I) is known for ages (Berichte 19) S. 636 (1886). It boils at 175° C. under atmospheric pressure, it is a colourless oily liquid. It is a strong irritant for the mucous membranes and for the skin. It is a labile compound, it has a tendency to decompose and polimerize with explosive violence.

The compound of the formula (I) may be prepared by chloromethylation using hydrochloric acid and formaldehyde, but considerable amount of heavily separable side product appears during the reaction (J. Amer. Chem. Soc. 64 (3) p 477 (1942)) and the yield of the reaction is weak (Org. Synth. Coll. 3 p 197 (1955)).

There were several attempts to increase the yield of the chloromethylation and the purity of the compound of the formula (I) thus obtained.

According to the U.S. Pat. No. 2,527,680 cold concentrated aqueous hydrochloric acid and cold aqueous formaldehyde solution were mixed, the mixture was saturated by hydrogen chloride gas and this was added gradually to the tiophene at −10° C. and the temperature of he reaction mixture was maintained below +1° C. The reaction mixture, which became biphasic after addition of water, was separated and the compound of the formula (I) was yielded by the fractional destination with a yield of 61.8%. Significant amount (20-28%) of side product was received, which was first of all bis-2-chloromethyl-tiophene and the target compound of the formula (I) was contaminated by this compound.

According to the U.S. Pat. No 4,501,903 dry hydrogen chloride gas was introduced into the mixture of tiophene, formaldehyde and concentrated hydrochloric acid at (−5° C.)-(−10° C.) during heavy stirring with a rate of 0.3-1.5 mol/mol tiophene/hour. After that the reaction mixture was diluted by water, it was left to stand at (−5° C.)-(−10° C.) and among the dividing phases the organic phase contained 60-75% compound of the formula (I). The yield of compound of the formula (I) fluctuated between 65-75%. The obtained compound of the formula (I) contained the following impurities: 2,5 dichloromethyl-thiophene, chloromethyl-bis-thienyl-methane, bis-thienyl-methane, thiophene and polimers.

The above impurities and 2-chloromethyl-5-hydroxy-methyl-thiophene, 3-chloromethyl-thiophene of formula (IV)

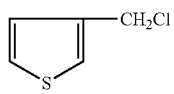

(IV)

and 2-thienyl-methanol are present in the thiophene products of formula (I) obtained by all processes known from the prior art.

The impurities listed make difficult the transformation of the non-isolated compound of the formula (I) into the compound of the formula (II), because they cause significant tar-production and the corresponding 3-cyano-derivative is a heavily separable impurity with a very close boiling point.

Furthermore the compound of the formula (IV) is transformed into the analogs of the API's syntheses and their separation during the syntheses or the resolution of the racemic API's or during the salt formation or the purification of the end products is extremely difficult. Therefore the amount of the 3-chloromethyl-thiophene of the formula (IV) and its cyano- or amine-derivative should be below the 0.3 mass % in the early intermediates (compounds of the formula (I), (II) and (III).

The isolation and the purification by vacuum distillation of the compound of the formula (I) is hazardous and not too efficient.

With this knowledge it was set as aim to find a process, which results a much purer compound of the formula (I) containing less than 0.3 mass % of 3-chloromethyl-thiophene of the formula (IV), the process makes avoidable the isolation of the compound of the formula (I) and results the preparation of the compound of the formula (II) containing no tar.

A further aim was to find a process, which eliminate the strong stirring, the appearance of a biphasic system and the emulsion during the process and remove the fluctuation of the yield depending on the rate of the introduction of hydrogen chloride gas.

An another aim was to increase the yield in comparison with the known processes and to find a process which can be scaled up without the deterioration of the quality of the product.

Unexpectedly it has been found that if the chloromethylation of the thiophene is carried out in the presence of a compound containing a keto-group, then a much purer compound of the formula (I) is yielded of which 3-chloromethyl-thiophene content is well below the 0.3 mass % limit and optionally in the presence of a compound containing a keto-group without disturbing tar-formation it can be transformed into the compound of the formula (II). The yield and the technical characters of this invented process fulfilled the aimed parameters.

According to the invention thiophene is chloromethylated in the presence of one or more compounds containing keto-group.

Preferably such compounds are applicable, which have a melting point below −15° C. and a boiling point below +250° C.

Such compounds are for example the dimethyl-ketone, diethyl-ketone, dipropyl-ketone, methyl-ethyl-ketone, methyl-propyl-ketone, methyl-isopropyl-ketone, methyl-butyl-ketone, methyl-isobutyl-ketone, methyl-terc.-butyl-ketone, methyl-pentyl-ketone and methyl-hexyl-ketone.

The chloromethylating agents used in the invented process are preferably concentrated aqueous hydrochloric acid, hydrogen chloride gas and formaldehyde or its polimers, for example the paraformaldheyde. The chloromethylation can be carried out in several ways according to the invention, for example thiophene is mixed with the compound containing keto-group and this mixture can be added to the mixture of concentrated aqueous hydrochloric acid and formaldehyde and then hydrogen chloride gas is introduced into the reaction mixture. It is also possible that the mixture of tiophene and the compound containing the keto-group is saturated with hydrogen chloride gas and then a mixture of formaldehyde and hydrochloric acid is added to it. This process variant is especially advantageous in case of large scale production.

The chloromethylation is carried out preferably between −15° C. and +20° C., the temperature range between 0° C. and +10° C. is the most advantageous. The molar ratio of the reagents and the thiophene corresponds to the usual ratio used during the chloromethylation, the following molar ratio is the most preferred:

thiophene:aqueous hydrochloric acid:hydrogen gas:paraformaldehyde=1,0:1,0-1,3:0,75-1,0:1,0.

The volumetric ratio of thiophene and the compound containing keto-group can be changed in a broad range preferred the ratio of 1:1-3 and the most preferred thiophene-keto-compound ratio is 1:2,0-2,6.

In case of some representatives of keto compounds it is advantageous to dissolve inorganic salts in the aqueous hydrochloric acid in order to help the breaking of the reaction mixture. The compound of the formula (I) can be isolated by procedure well known in the art or without isolation after setting the pH of the reaction mixture to neutral it can be transformed by well-known organochemical methods into the compound of the formula (II) preferred procedure is a reaction with alkaline metal cyanides, for example with sodium cyanide or potassium cyanide, optionally in the presence of a phase transfer catalysator (for example tetra-butyl-ammonium halogenides).

The compound of the formula (II) can be isolated by methods known per se.

The compound of formula (II) may be transformed into the amine of the formula (III) and into different API's.

Further details of the present invention are illustrated by the following examples without restricting our claim to them.

Figure 2:
Figure 3:
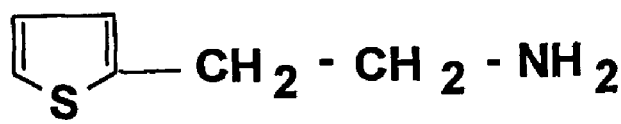
Figure 4:
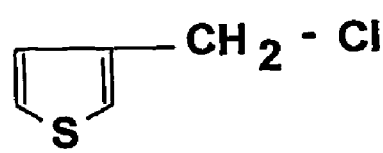

FIG. 1 shows formula (I),
FIG. 2 shows formula (II),
FIG. 3 shows formula (III) and
FIG. 4 shows formula (IV).

EXAMPLES

Example 1

Into the suspension containing 84 g (1 mol) of thiophene, 168 g of methyl-isobutyl-ketone, 100 g (1 mol) of aqueous hydrochloric acid (37%) and 30 g (1.0 mol) of paraformaldehyde (Manufacturer: Degussa, number of monomeric units is between 4-98) at 0° C.-(+5° C.) during 6 hours 36.5 g (1 mol) of hydrogen chloride gas was introduced. After stopping the gas introduction the reaction mixture was stirred over a period of 1 hour 0° C.-(+5° C.). After that the reaction mixture was diluted with 90 g of water, the organic phase was washed with 50 g of 20% potassium carbonate solution to the neutral pH. The composition of the reaction mixture was determined by gas chromatography and was the following (area %): thiophene 30.3%, 2-chloro-methyl-thiophene 61%, 3-chloromethyl-thiophene 0.2%, 2,5dichloromethyl-thiophene 1.1%, bis-thienyl-methane 6.7%, chloromethyl-bis-thienyl-methane 0.2%.

The non-reacted thiophene (25 g) and the methyl-isobutyl-ketone were removed in vacuum by distillation.

The amount of the obtained crude 2-chloromethyl-thiophene is 75 g (81%).

Example 2

In the mixture of 84 g (1 mol) of thiophene and 168 g of methyl-isobutyl-ketone (their volumetric ratio is 1:2.5) between 0° C. and 15° C. 27.3 g (0.75 mol) of hydrogen chloride were absorbed. In 130 g (1.25 mol) 37% of aqueous hydrochloric acid, 30 g (1 mol) of paraformaldehyde were dissolved (Manufacturer: Degussa, number of monomer units is between 4-98) at 60° C. and the solution was cooled to 20-25° C. and this mixture was added to the mixture containing thiophene over a period of 4-6- hours between 0° C.-(+5° C.). After the end of feeding the mixture was diluted with 90 g of water and the organic phase was separated and it was wasted with 50 g of 20% potassium carbonate solution. The non-reacted thiophene, 24 g and the methyl-isobutyl-ketone were removed by vacuum-distillation and 74.1 g (80%) of 2-chloromethyl-thiophene were received. Its quality was the same as in case of the product of Example 1.

Example 3

All steps were identical with the procedure described in Example 1 but instead of methyl-isobutyl-ketone 168 g of acetone were used and for the breaking of the reaction mixture 90 g of 30 mass % of calcium chloride solution were used because of the solubility of the acetone 74.6 g (80.5%) of 2-chloromethyl-thiophene were obtained, its quality was the same as in case of the product of Example 1.

Example 4

All steps were identical with the procedure of Example 3 but instead of acetone 168 g of methyl-ethyl-ketone were used. 74.3 g (80.2%) 2-chloromethyl-thiophene were obtained. Its quality was the same as in case of the product of Example 1.

Example 5

All steps were identical with the procedure of Example 1 but 30 g of calcium chloride were dissolved in 100 g of 37% aqueous hydrochloric acid. Thus the addition of 90 g of water was not necessary and the washing to neutral pH was carried out immediately. 74.1 g (80%) of 2-chloromethyl-thiophene were obtained, its quality was the same as in case of the product of Example 1.

Example 6

Preparation of 2-thienyl-acetonitrile of the formula (II) without the isolation of 2-chloromethyl-thiophene of the formula (I)

The crude 2-chloromethyl-thiophene obtained according to Example 1 washed with 20 mass % of potassium carbonate to neutral pH and separated from the non-reacted thiophene and the methyl-isobutyl-thiophene was added to 49 g (1 mol) of sodium cyanide and 4 g of tetrabutyl-ammonium-bromide, both dissolved in 150 g of water at 60° C. The mixture was stirred at 70° C. for 4 hours and then 160 g of water were added thereto, at 40° C., the aqueous and the organic phase were separated. The upper organic phase was washed twice with 50 g of water and the ketone-thiophene mixture was removed by distillation.

Thus 64 g (68%) of distilled 2-thienyl-acetonitrile were obtained, which had the following composition in area % measured by gas chromatography:

| | |
|---|---|
| 2-thienyl-acetonitrile | 87.7% |
| 3-thienyl-acetonitrile | 0.2% |
| 2-thienyl-alcohol | 3.7% |
| 3-thienyl-alcohol | 0.2% |
| methyl-isobutyl-ketone | 0.4% |
| bis-thienyl-ethane | 1.8% |

From the above crude product a 2-thienyl-acetonitrile product with 99.5% purity was obtained in which the 3-thienyl-acetonitrile content is 0.1%.

The invention claimed is:

1. A process for the preparation of a compound of formula (I):

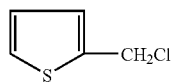
(I)

by chloromethylation of thiophene, using aqueous concentrated hydrochloric acid, gaseous hydrogen chloride and paraformaldehyde, in the presence of one or more dialkyl-ketone type solvents.

2. A process according to claim 1 wherein the chloromethylation is carried out in acetone or methyl-ethyl-ketone or methyl-isobutyl-ketone.

3. A process according to claim 1 wherein the chloromethylation is carried out between −15° C. and +20° C.

4. A process according to claim 1 wherein the gaseous hydrogen chloride is introduced into the reaction mixture or is used after absorption in the dialkyl-ketone type solvent.

5. A process according to claim 1 wherein the molar ratio of thiophene, aqueous hydrochloric acid, gaseous hydrogen chloride and paraformaldehyde is 1.0:(1.0-1.3):(0.75-1.0) 1.0.

6. A process according to claim 1 wherein 1 to 3 volumes of the dialkyl-ketone type solvent are used per volume of thiophene.

7. A process according to claim 1 wherein the compound of formula (I) is reacted with aqueous alkali cyanide optionally in the presence of a phase-transfer catalyst to give a compound of formula (II)

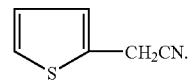
(II)

8. A process according to claim 6 wherein 2.0 to 2.6 volumes of the dialkyl-ketone type solvent are used per volume of thiophene.

* * * * *